United States Patent
Decote

(10) Patent No.: US 10,568,780 B2
(45) Date of Patent: Feb. 25, 2020

(54) 24-HOUR INCONTINENCE DETECTION SYSTEM, SINGLE TRANSISTOR LIQUID LEAK DETECTOR CIRCUIT AND METHOD OF OPERATING THE LIQUID LEAK DETECTOR CIRCUITS

(71) Applicant: Robert Decote, Hollywood, FL (US)

(72) Inventor: Robert Decote, Hollywood, FL (US)

(*) Notice: Subject to any disclaimer, the term of this patent is extended or adjusted under 35 U.S.C. 154(b) by 0 days.

(21) Appl. No.: 16/034,622

(22) Filed: Jul. 13, 2018

(65) Prior Publication Data
US 2019/0282412 A1   Sep. 19, 2019

Related U.S. Application Data

(60) Provisional application No. 62/642,321, filed on Mar. 13, 2018.

(51) Int. Cl.
*A61F 13/42* (2006.01)
*G01M 3/16* (2006.01)
*G08B 5/22* (2006.01)
*G08B 21/20* (2006.01)

(52) U.S. Cl.
CPC ............. *A61F 13/42* (2013.01); *G01M 3/16* (2013.01); *G08B 5/223* (2013.01); *G08B 21/20* (2013.01); *A61F 2013/424* (2013.01)

(58) Field of Classification Search
CPC ......... A61F 13/42; G08B 21/20; G08B 5/223; G01M 3/16
See application file for complete search history.

(56) References Cited

U.S. PATENT DOCUMENTS

| | | | | |
|---|---|---|---|---|
| 4,205,672 | A | | 6/1980 | Dvorak |
| 4,754,264 | A | * | 6/1988 | Okada ........................ A61F 5/48 340/573.5 |
| 5,557,263 | A | * | 9/1996 | Fisher ........................ A61F 5/48 128/886 |
| 6,009,757 | A | * | 1/2000 | LeComte .............. G01L 9/0075 361/283.4 |
| 6,639,517 | B1 | * | 10/2003 | Chapman ................ G01M 3/16 137/312 |
| 9,931,251 | B2 | * | 4/2018 | Euliano .................... A61F 13/42 |
| 2005/0270162 | A1 | * | 12/2005 | Hsieh ...................... A61F 13/42 340/573.5 |
| 2010/0030167 | A1 | * | 2/2010 | Thirstrup ................ A61F 5/445 604/318 |
| 2014/0266735 | A1 | | 9/2014 | Riggio et al. |

\* cited by examiner

*Primary Examiner* — David Z Huang

(74) *Attorney, Agent, or Firm* — Laurence A. Greenberg; Werner H. Stemer; Ralph E. Locher

(57) ABSTRACT

A 24-hour incontinence detection system contains a conductivity sensor being a passive device and is disposed in a vicinity of where a leak is most likely to occur. A liquid leak detection circuit is connected to the conductivity sensor and receives a resistance value sensed by the conductivity sensor. A Bluetooth transmitter is connected to the liquid detection circuit. An alarm receives a signal from the Bluetooth transmitter. The signal is representative of the output from the liquid leak detection circuit. The liquid leak detection circuit activates the alarm in dependence on the resistance value of the conductivity sensor.

10 Claims, 4 Drawing Sheets

24-HOUR INCONTINENCE DETECTION SYSTEM, SINGLE TRANSISTOR LIQUID LEAK DETECTOR CIRCUIT AND METHOD OF OPERATING THE LIQUID LEAK DETECTOR CIRCUITS

CROSS-REFERENCE TO RELATED APPLICATION

This application claims the priority, under 35 U.S.C. § 119, of provisional patent application Ser. No. 62/642,321, filed Mar. 13, 2018; the prior application is herewith incorporated by reference in its entirety.

BACKGROUND OF THE INVENTION

Field of the Invention

The invention relates to leak detection devices and their specific uses.

Incontinence leaks affect all infants and many seniors. With infants, the situation usually improves with advancing age whereas with seniors it usually worsens. The first line of defense for infants and seniors alike is the ubiquitous passive retention device called a diaper, which has been in worldwide use for countless years.

Fairly recently, some pro-active devices have been developed for infants, such as diapers with built-in leak detectors and other devices of one sort or another. However, these devices have significant shortcomings. First, they are designed exclusively for use on infants. Second, they are designed to detect either urinary or fecal leaks, but not both simultaneously. Third, they are relatively expensive. Fourth, they are not designed for 24-hour use, in particular, for ambulatory seniors. Fifth, they offer seniors no level of discreetness. Discreetness is an important feature for seniors because incontinence frequently causes seniors to withdraw from living a full social life, in order to avoid experiencing embarrassing leaks.

SUMMARY OF THE INVENTION

It is accordingly an object of the invention to provide a 24-hour incontinence detection system and a single transistor liquid leak detector circuit that overcome the above-mentioned disadvantages of the prior art devices of this general type.

With the foregoing and other objects in view there is provided, in accordance with the invention, a 24-hour incontinence detection system. The detection system contains a sensor assembly having a conductivity sensor being a passive device and disposed in a vicinity of where a leak is most likely to occur, a liquid leak detection circuit connected to the conductivity sensor and receives a resistance value sensed by the conductivity sensor, and a Bluetooth transmitter connected to the liquid leak detection circuit and transmits a signal being representative of an output of the liquid leak detection circuit. An alarm is coupled to the sensor assembly and receives the signal via the Bluetooth transmitter. The alarm is activated in dependence on the signal.

As presented here, the invention provides 24-hour electronic incontinence monitoring for seniors and infants alike by utilizing two different system configurations; (1) a daytime configuration, which provides ambulatory seniors with a means for promptly and discreetly detecting incontinence leaks, and (2) a slumber-time configuration which provides seniors with a wake-up call for promptly responding to incontinence leaks while asleep.

In addition, the slumber-time system configuration of this invention can provide caretakers of infants and bedridden incontinent seniors alike with a means for promptly responding to leaks on a 24-hour monitoring basis.

In addition, both system configurations can promptly and simultaneously monitor for both urinary and fecal leaks.

In addition, the single transistor leak detector circuit, which is the novel cornerstone of this invention, may be used in many other applications and configurations.

In accordance with an added feature of the invention, the conductivity sensor has two metal plates with a gap disposed therebetween. The gap and any liquid disposed in the gap define the resistance value.

In accordance with an additional feature of the invention, the conductivity sensor has two conductor cables connected to the liquid leak detection circuit.

In accordance with another feature of the invention, the liquid leak detection circuit includes an input connected to the conductivity sensor and has first and second connector points, a transistor connectable to a DC voltage source and has a base node, an emitter node and a collector node, a first resistor connected between the transistor and the first connector point, and a second resistor connected between the transistor and ground. The liquid leak detection circuit further has a Zener diode disposed between the transistor and ground and a light emitting diode is disposed between the second resistor and the ground.

In accordance with another added feature of the invention, there is a Bluetooth receiver connected to the alarm and receives the signal from the Bluetooth transmitter.

In accordance with yet another feature of the invention, the liquid leak detection circuit has only one transistor.

In accordance with an added additional feature of the invention, the sensor assembly has a circular shaped, non-conductive substrate being less than 1 inch in diameter and supporting all components of the sensor assembly. The circular shaped, non-conductive substrate has a back side opposite a component side, the back side has a hook-and-loop material for assisting in attaching the sensor assembly to an undergarment.

In accordance with a further feature of the invention, the alarm is a cell phone, a smartphone, a specially designed Bluetooth receiver which resembles a cell phone, a vibrator or a sound box.

In accordance with a further added feature of the invention, the conductivity sensor is one of two conductivity sensors connected to the liquid leak detector circuit.

The user of this system (called the "wearer"), attaches a hook and loop (e.g. VELCRO) backed sensor assembly of about ½" in diameter to his undergarment, or diaper, close to where the incontinence leakage (hereafter called "leakage") is expected to occur. Owing to the sensor assembly's small size and light weight, the wearer can move about freely, completely unencumbered.

As soon as a leakage occurs, an electronic integrated circuit (IC) detects it and triggers a Bluetooth radio frequency (RF) transmitter. The wireless transmitted signal causes an alert to occur such as the wearer's portable phone to ring or an alarm to sound. Upon answering the phone, the wearer discreetly recognizes the source of the call, turns his/her phone off, excuses himself/herself and heads for the nearest restroom to privately tend to his/her situation (or the caretaker proceeds to change the diaper, etc.).

After the sensor is removed, cleaned and dried with a piece of tissue paper, it is reattached to a new undergarment and is immediately ready for the next detection of leakage.

When a leakage is detected, not only is a Bluetooth signal transmitted to the phone of the wearer, but a red light-emitting-diode (LED), mounted directly on the sensor assembly, immediately turns on indicating moisture detection. And, once the sensor is properly wiped dry, the LED turns off, providing visible confirmation that the sensor is sufficiently dry, and ready for re-use.

The illustrative leakage detector circuit presented below and its companion Bluetooth transmitter (both tiny ICs) call for a 9-Volt battery which, using currently available batteries will be too large to fit onto the small sensor assembly. Therefore, it will be necessary to either; (a) have the wearer also wear a waistband with a built-in pocket for a battery, (b) use a source of suitably small 9-volt batteries, or (c) redesign the illustrative example so that it functions with a lower DC voltage. We hasten to add that implementing any of these power supply options will not affect the sensor assembly's portability or functionality.

Although the invention is illustrated and described herein as embodied in a 24-hour incontinence detection system and a single transistor liquid leak detector circuit, it is nevertheless not intended to be limited to the details shown, since various modifications and structural changes may be made therein without departing from the spirit of the invention and within the scope and range of equivalents of the claims.

The invention will be explained in more detail based on the appended figures. In the figures, elements and components that correspond to one another have the same reference symbols. For more clarity, the figures have not been drawn to scale.

DETAILED DESCRIPTION OF THE INVENTION

Figure 1:
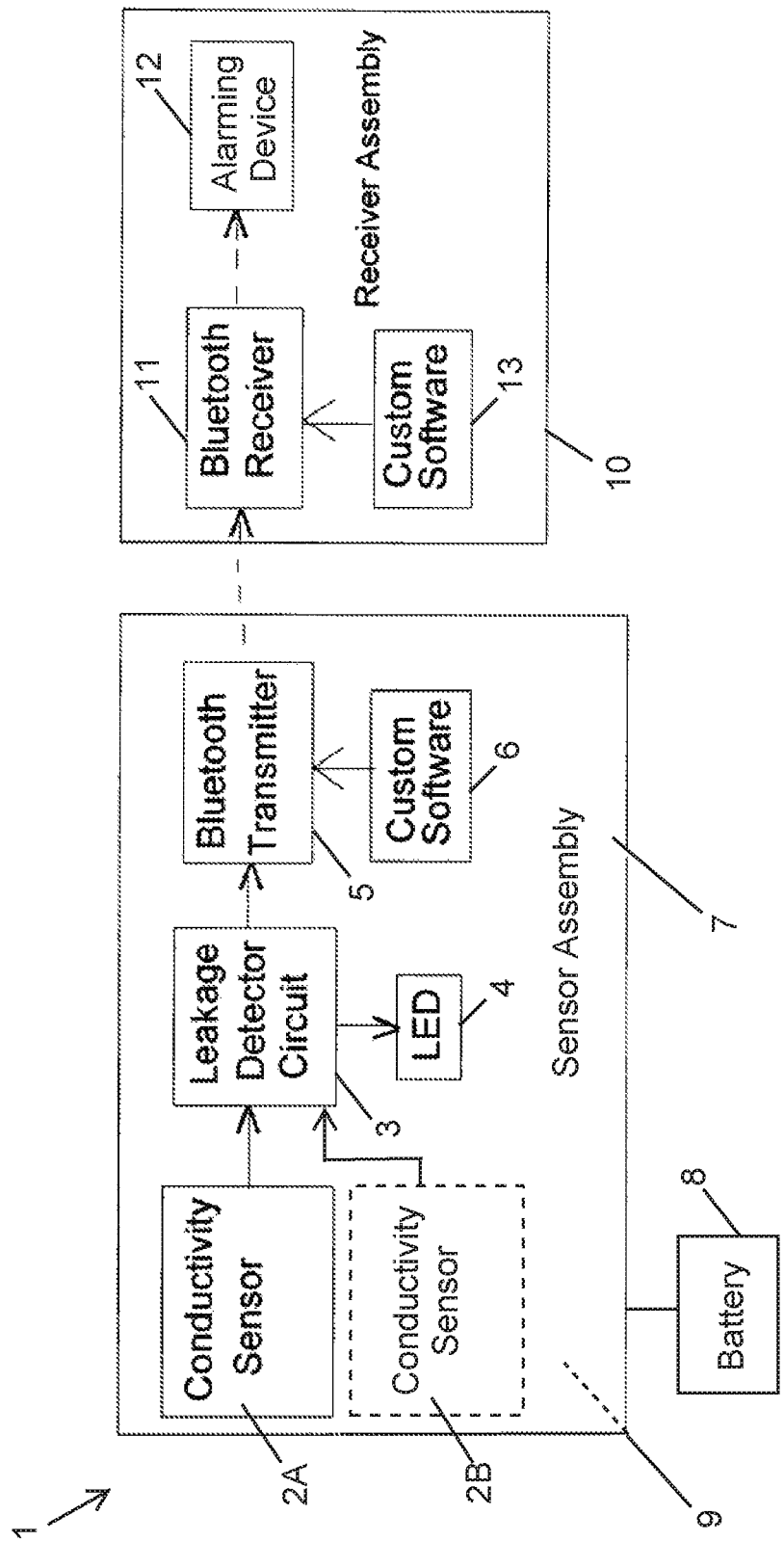
FIG. 1 is a block diagram of a 24-hour incontinence detection system according to the invention.

Referring now to the figures of the drawings in detail and first, particularly to FIG. 1 thereof, there is shown a block diagram of a 24 hour incontinence detection system (hereafter leakage detection system). In the broadest possible terms, the leakage detection system is composed of two major assemblies; a sensor (or 'transmitting') assembly 1 which, thanks to integrated circuit (IC) technology, can be less than one inch in diameter and is worn by the user continuously (e.g. 24 hours), and a receiver (or 'responding') assembly 10; which must be of a portable configuration for daytime use or of a stationary configuration for slumber-time use, or whenever portability is not required.

As shown in FIG. 1, the sensor assembly 1 has a conductivity sensor 2A, 2B, a leak detector circuit 3, a light emitting diode (LED) 4, a Bluetooth transmitter 5 and running custom software 6. Ideally, the sensor assembly 1 has a base 7 formed as a plastic disk on the order of ½-1½ inch diameter, preferably less than 1 inch. Other shapes such as square or rectangular are possible and of course other sizes, however, a small compact base 7 is preferred. A battery 8 is provided for providing energy to the sensor assembly 1. The sensor assembly 1 is ideally fabricated with a hook-and-loop material 9 such as VELCRO on its reverse side for assisting in attaching the sensor assembly to an undergarment.

The receiver assembly 10 has a Bluetooth receiver 11, a portable alarm 12 and also running custom software 13.

System action begins with one or two conductivity sensor assemblies 2A, 2B, which is/are placed close to where leakages are likely to occur. For example, one sensor 2A may monitor for urinary leaks and, if required, the other sensor 2B may be used to monitor for fecal leaks.

Figure 2:
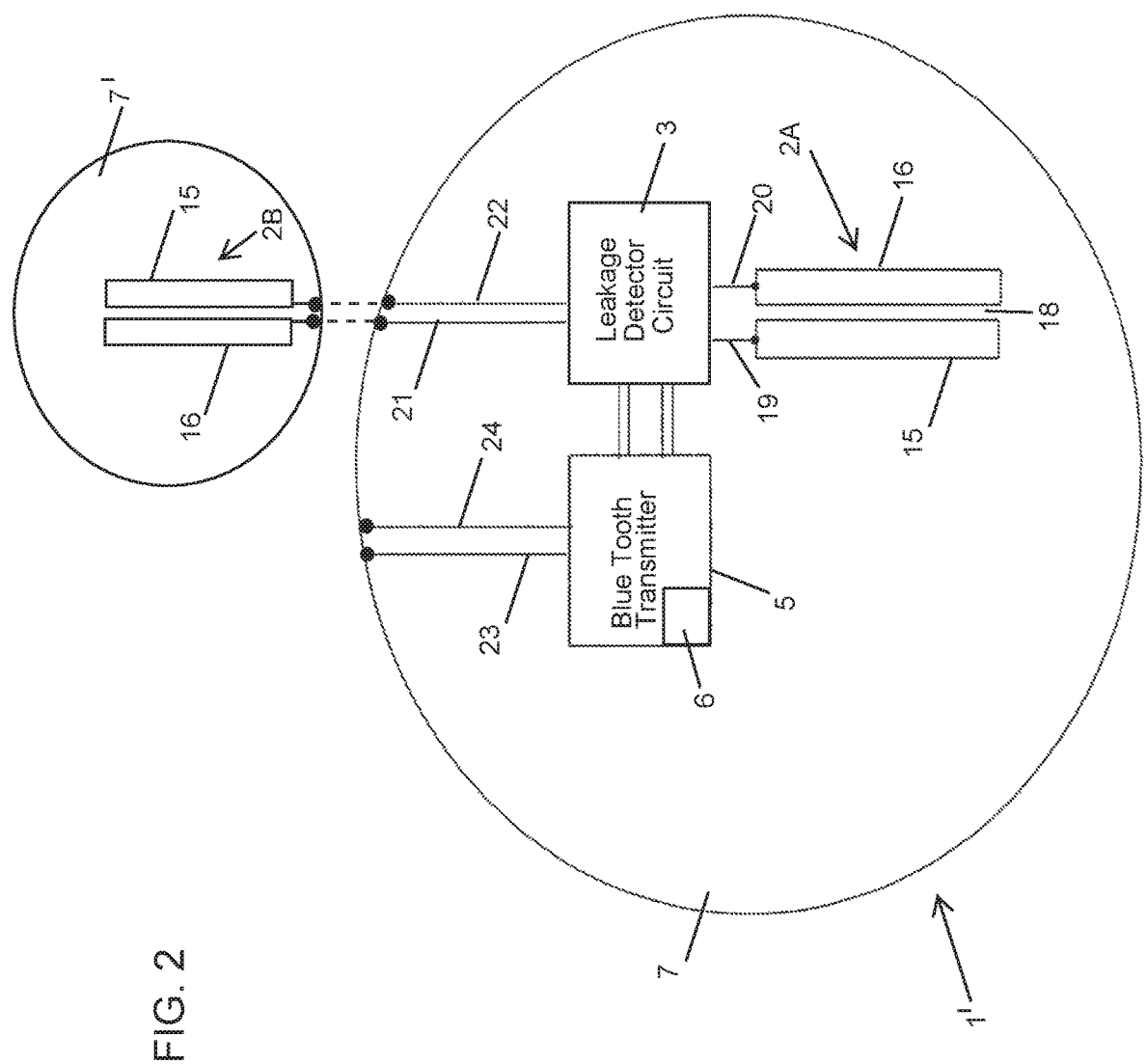
FIG. 2 is a block diagram of a further embodiment of a sensor assembly.

FIG. 2 shows a further sensor assembly 1' similar to that of the sensor assembly 1 shown in FIG. 1. The further sensor assembly 1' contains the conductive sensor 2A, the leak detector circuit 3 with a LED 4 included and the Bluetooth transmitter 5. The conductivity sensor 2A has two narrow metal plates 15, 16 (typically copper or stainless steel) which are mounted on the non-conductive substrate 7 (typically plastic and circular in shape). The gap 18 between the metal plates 15, 16 is where the electrically conductive leakage is to be sensed. Note that there is a wire 19, 20 attached to each of the metal plates 15, 16; the other ends of these wires connect to an input port RG1 of the leak detector circuit 3, as discussed below. Also note that the leak detector circuit 3 has two further leads 21, 22 from a miniature jack on the sensor assembly's edge; they lead to another input port RG2 of the leak detector circuit 3. When two sensors 2A, 2B are to be used, the sensor 2A will be disposed on an active sensor assembly because it contains all of the electronics and software, whereas the other sensor 2B will be a remote, passive sensor as it will consist of only a pair of conductive sensor plates 15, 16 mounted on a similar disc-shaped substrate 7' and fed to a miniature jack at its edge. Thus, we can say that the remote, passive sensor 2B gets "plugged into" the active sensor assembly, when two sensors 2A, 2B are required.

Also shown in FIG. 2 is an IC which contains the Bluetooth transmitter circuitry 5 and its custom software 6. Clearly, it gets its input from the leak detector circuit 3 and both ICs 3, 5 get their DC power from an external battery 8 via the other miniature jack 23, 24.

The key feature of the conductive sensor 2A, 2B is the gap 18, where the conductivity of a fluid, such as urine in this example, is to be sensed. As the gap 18 fills with fluid, the increasing conductivity in the gap 18 results in a decreasing electrical resistance in the leak detector circuit.

All electrically cognizant people are thoroughly familiar with Ohm's Law; but, as a rule, they seldom encounter the terms conductivity and resistivity. Therefore, a brief review of their definitions, relationships and related equations is now presented.

Start by noting that a homogeneous material's electrical conductance ($\sigma$) is expressed in Siemens, or Ohm-cm$^{-1}$. We also note that electrical resistivity, Rho ($\rho$), in Ohm-cm, is the reciprocal of its electrical conductance.

It's a given that we can calculate the electrical resistance R presented by a homogeneous block of any material by using the equation; $R = \rho L/A$. This formula states something we can intuitively feel is correct; i.e., that for the stated parameter ($\rho$), the net resistance will be proportional to its length (L) and inversely proportional to its conductive cross-sectional area (A).

Finally, in order to firmly grasp these parameter's dimensions, we see that when we solve for p from the above equation, we get, $\rho=RA/L$, from which it follows that its units are Ohm-cm, and that the corresponding dimension for conductivity is Ohm-cm$_{-1}$.

Figure 3:
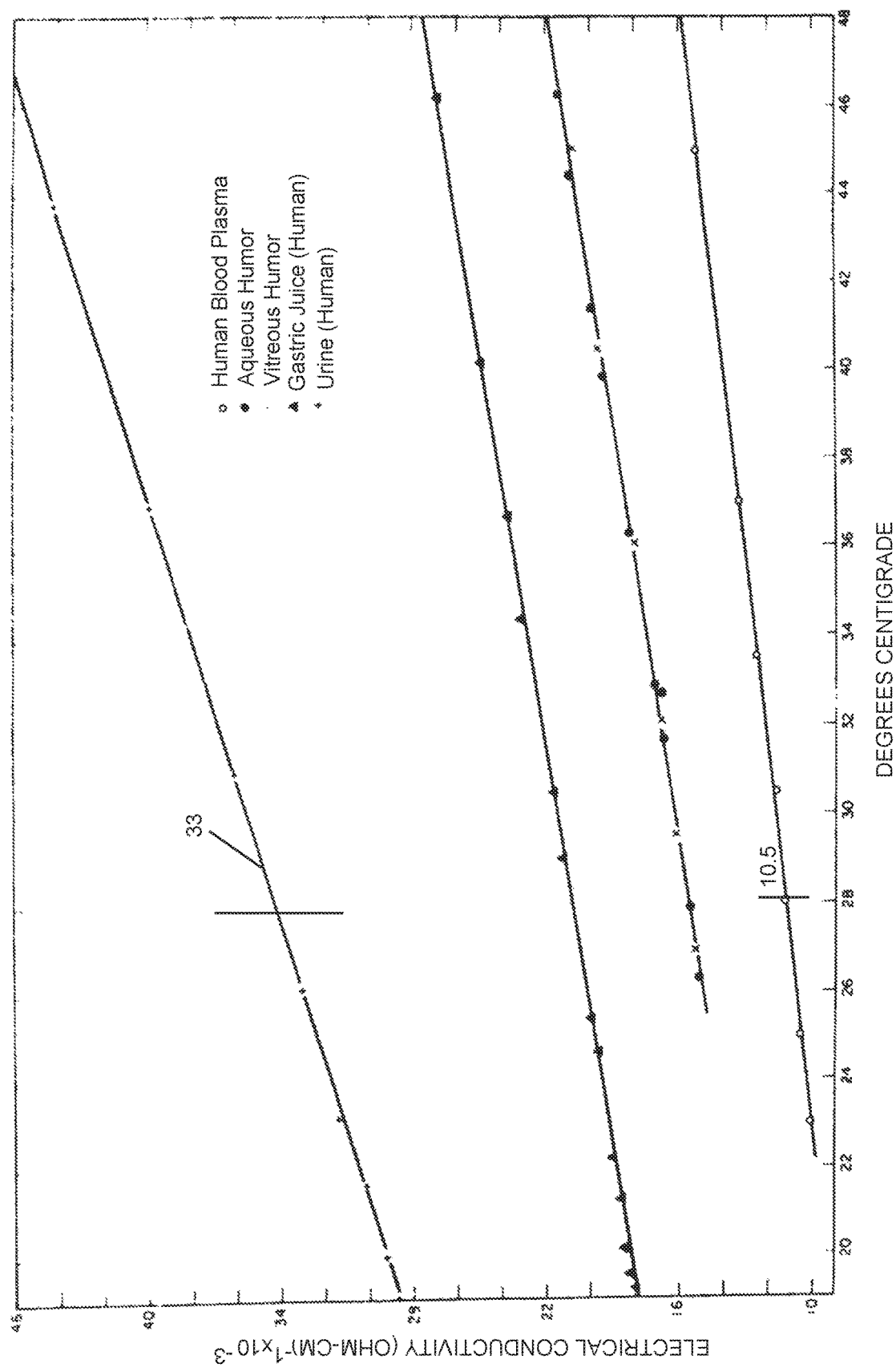
FIG. 3 is a graph showing published curves for electrical conductivity of certain fluids.

These are the not-too-familiar parameters we must deal with at this point because FIG. 3 presents published conductivity curves for four common liquids, one of which is human urine 33, which curve shows the conductivity of urine at 28° C. (approximately 80° F.) to be approximately $33\times10^{-3}$ Ohm-Cm$^{-1}$. Therefore, the resistivity of urine is $\rho$–urine=$1/(33\times10^{-3})$ Ohm-cm$^{-1}$=1 Ohm-cm/$(33\times10^{-3})$ =30.3 Ohm-cm.

For our illustrative example we select a set of reasonable dimensions for the sensor's gap, as follows; let us assume the sensor's plates are of copper which is 1/16" thick, the gap is 1/2" long and the gap's width is 1/32".

The next step is to convert those dimensions to centimeters, for which we get:
a) Electrical path length: 1/32"=(1/32)"×2.54 cm/in.=0.079 cm;
b) Gap's metal height: 1/16"=(1/16)"×2.54 cm/in.=0.159 cm; and
c) Gap's metal length: 0.5"=(0.5)"×2.54 cm/in.=1.27 cm.

So, for the specified gap we have; L=0.079 cm, and the electrical cross-sectional area (A) is the product of the other two dimensions=0.159 cm×1.27 cm=0.202 cm$^2$.

And, using the resistance equation, $R=\rho(L/A)$, we get:
a) Rgap-urine=(30.3 Ohm-cm)×(0.079 cm/0.202 cm$^2$)=11.9 Ohms.

In essence, the conductivity sensor 2A or 2B specified above presents an essentially open circuit when the gap 18 is dry and a resistance of approximately 12 Ohms when the gap 18 is filled with urine. This data is used in the discussion of the electronic detector circuit 3, below.

Figure 4:
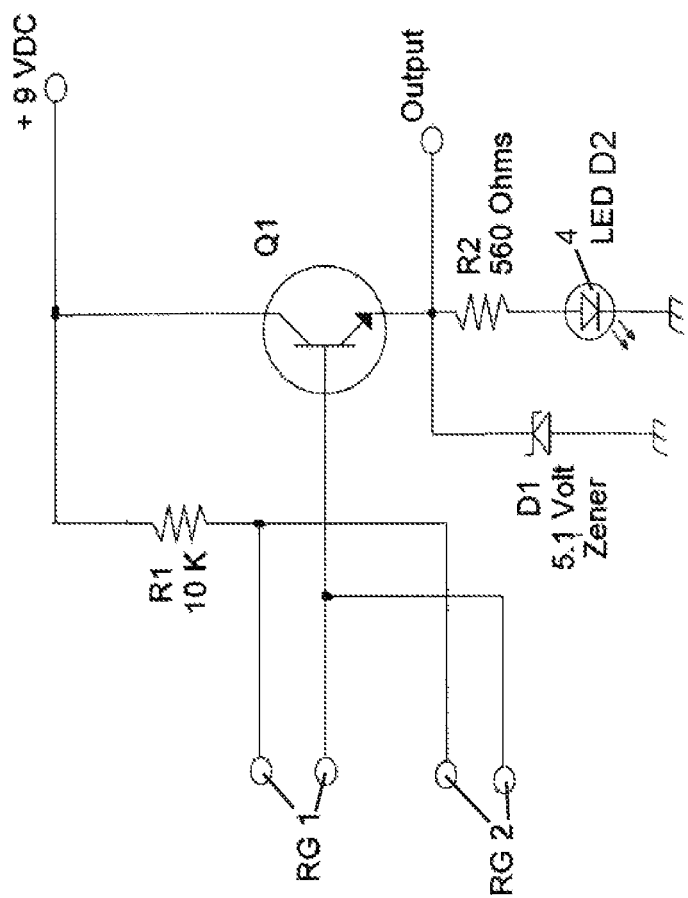
FIG. 4 is a circuit diagram of a single transistor NPN leak detector circuit.

A configuration of the leak detector circuit 3 is shown in FIG. 4 which shows a schematic diagram for a single-transistor NPN leak detector circuit 3, which is to be built as a tiny integrated circuit (IC) chip.

At the left of the diagram of FIG. 4, we see two sensor-gap input ports RG1, RG2 which are wired in parallel between a VDC power supply line and a base of transistor Q1, both of which are in series with resistor R1. The resistor R1 is a 10K-Ohm current-limiting resistor. It is included so that if a short circuit ever occurs between its input terminals, Q1's base current will be limited to a current flow of something less than 1 milliamp; not enough to damage Q1.

The two sensor inputs RG1, RG2 are present in FIG. 4 because: (a) in some applications it will be required to monitor for both urinary and fecal incontinence simultaneously, and (b) to call attention to the fact that a single detector circuit may have multiple input ports; more about that below. It is understood at this time that the leakage detection circuit 3 can function with only one sensor input RG1 (urine) and the second sensor input RG2 (fecal) requires the use of the second conductivity sensor 2B.

When both sensor inputs RG1, RG2 are non-conducting (dry) an open-circuit exists between the supply voltage and Q1's base, so there will be no base-emitter current into Q1. As a result, only a negligible amount of transistor leakage current (in the range of 50 nano-amps) flows through resistor R2, to ground via the LED 4.

We express this in a shorthand manner as:
Rg-dry→Q1's Ib=0→Q1 is cut-off→No current thru R2→Output=0 VDC.

This statement will be true regardless of what transistor is selected, so we simply hold it in abeyance while we proceed to analyze the leakage detector circuit's conductive state.

The selected transistor is a 2N3904 (NPN), whose salient characteristics, are:

a) VCBO Collector-Base Voltage (Ie=0)=60 V;
b) VCEO Collector-Emitter Voltage (Ib=0)=40 V;
c) VEBO Emitter-Base Voltage (Ic=0)=6 V;
d) ICO Collector Cutoff Current=50 nAdc;
e) ICsat Collector Saturation Current=200 mA; and
f) hfe_min, DC Current Gain (Ic=1 mA)=80, min.

At this time we note that this is merely representative of one type of transistor Q1 that may be used and many other transistors may be substituted—PNPs, FETs, IGBTs, etc.

The selected LED 4 is a surface-mounted Brightek QBLP1515-R5 whose salient characteristics are:
a) Color: Red;
b) Typical Fwd Voltage Drop @5.0 mA: 2.0 VDC;
c) Surface area: approx. 1.5 mm×1.6 mm; and
d) Depth: approx. 1 mm.

Since the LED 4 has a voltage drop of 2.0 Volts at 5.0 ma and it is in series with a 560 Ohm resistor R2, we see that in order to get 5.1 VDC at Q1's emitter, the equation that relates to this set of conditions is:

$$5.1 \text{ VDC}=2.0 \text{ VDC}+560\times Ie.$$

So that, Ie=(3.1V/560)=5.5 mA, which is close enough for our purpose, as evidenced below.

From the circuit diagram and discussion presented above, it's apparent that as the sensor's gap 18 gets wet with leaked urine, its resistance (Rg) will decrease from 'infinity' (an open circuit), down, to a minimum of 12 Ohms, and that somewhere before that, Q1 will conduct enough current to reach the detection or "Trigger" value of +5.1 VDC output. Please note that the Zener diode D1 clamps the output voltage to 5.1 volts. We will now calculate what that critical value ($Rg_{Trigger}$) is.

As shown above, the selected transistor has a minimum current gain (hfe_min) of 80@Ic=1 mA, so a conservative value for current gain at 5.5 mA may be about 70; therefore the base current required to obtain that level of conduction comes to (5.5 mA/70)=0.079 mA, or 79 pA.

The next step is to examine the transistor's base-drive current path at the detector's trigger point. Allowing for a Veb drop=+0.7 VDC, the related equation is:

$$9 \text{ VDC}=(79\times10^{-6})(Rg+10K)+0.7 \text{ VDC}+5.1 \text{ VDC}$$

$$(9V-5.8V)=(79\times10^{-6})(Rg+10K)$$

$$3.2/(79\times10^{-6})=Rg+10K$$

$$0.041\times10^{6}=Rg+10K$$

$$Rg_{Trigger}=31K.$$

So, once the gap resistance decreases from an open circuit to 31K Ohms, there will be enough base current to provide an output emitter voltage of +5.1 volts. And, since the calculation above shows that with the gap 18 filled with urine, the gap's resistance is only 12 Ohms, we see that we have a ratio of (31,000/12)=2,583 of "overdrive" in order to trigger the detector.

In other words, the detector will be tripped when it is only 0.04% wet. If it turns out to be too sensitive, the sensor's gap geometry can be re-designed, a different transistor can be selected and/or the location of the sensor on the wearer's undergarment can be changed. However, it seems that an early leak detection capability is desirable feature.

The proposed incontinence detector system is viable, and not only for urine, but for many other liquids, including blood (whose resistivity is somewhere between 4 and 5 times that of urine).

We pause here to mention that if the liquid whose leaks we want to detect in some other application proves to be essentially non-conductive, the sensor can be easily primed by sprinkling salt, or placing a fraction of a salt tablet, in close proximity to the sensor gap 18. Therefore, it seems safe to say that almost any liquid leak can be detected with the above design.

Finally, the sensor assembly 1 has the Bluetooth transmitter 5 for transmitting an alert to the receiver assembly 10 that a liquid has been detected. The Bluetooth transmitter 5 is formed from digital circuitry which, with zero volts input, produces zero volts output. But, as soon as its input rises to +5.1 VDC, it becomes activated, i.e., its custom software causes it to transmit a properly encoded wireless signal to the nearby Bluetooth receiver 11.

In summary, the sensor assembly 1 consists of the following three sub-assemblies:

a) The conductivity sensors 2A, 2B which each consist of the two metal plates 15, 16 with the well defined gap-geometry 18 and the two wires 19-22 which connect it to the leak detector circuit 3. Its role is to provide the leak detector circuit 3 with a net resistance whose value decreases as it senses moisture; ranging from an open circuit, to a value low enough to 'trigger' the leak detector circuit 3.

b) The leak detector circuit 3 is a single-transistor circuit, best fabricated as an integrated circuit in this application, designed to provide 0 VDC when the sensor's gap is dry, and an output voltage of +5.1 VDC when the sensor's gap resistance falls to, or below, a certain 'trigger' level. As a desirable feature, it also turns on the LED 4 when wetness is detected. We note, in passing that energizing the LED 4 does not impose any additional current load as it uses the current which produces the +5.1 VDC output.

c) The Bluetooth transmitter 5 is a standard "off-the-shelf" integrated circuit. It is normally turned off, awaiting a +5.1 VDC signal from the leakage detector circuit 3. Upon sensing the activation voltage, it transmits a message e.g. a phone call to the wearer's portable notification or alarming device 12 such as a phone. Note that some digital circuit and software design is called for at this point in order to transmit the desired message. At this point we note that all of these sub-assemblies are small enough to be mounted on the small plastic substrate 7 and constitute the wearable sensor assembly 1.

We now turn our attention to the receiver assembly 10. The alarming device 12 is ideally a portable cell phone, a smart-phone, or a Bluetooth receiver resembling a cell phone. Alternatively for daytime use, a Bluetooth activated electro-mechanical vibrator—silent, and small enough to fit in a pocket or purse but vigorous enough to be readily felt by the wearer may be used. Such devices are commercially available, with a self-contained battery.

For slumber time use, a customized Bluetooth activated sound-box can be used. It will be powered from a standard 120 VAC wall-mounted outlet. The sound-box may have a volume control and it may also include circuitry suitable for recharging the sensor assembly's battery. If desired, a relay may be included so that when the sound-box is activated, a night-light, or other device, will also turn on.

On the other hand, for a stationary receiver alert configuration, there are several other possibilities, such as a relay controlled night lamp, a USB output to a computer, etc. We also mention that the stationary device can be powered from a ubiquitous 120 VAC power outlet, so it can also incorporate a battery-charging station.

In sum, the configuration of the sensor assembly 1 is pretty much frozen whereas the receiver assembly 10 can be portable or stationary and can be readily designed to suit numerous applications, including monitoring networks, as discussed below.

The components of this system lend themselves readily too many other leak detection applications, some of which are mentioned below.

Hospital ward monitoring: In many hospitals and clinics, several patients in post-op rooms can be simultaneously monitored for blood leakages and/or incontinence leakages. And such detected leakages can be fed to a computer for a nurse's prompt response, to document a patient's medical history or for research studies.

Parental monitoring of infants or caretaker monitoring of bed-ridden persons: This most welcome alarm system was mentioned above.

Household appliance monitoring: Because one detector circuit can monitor any number of sensors simultaneously, the single transistor leakage detector circuit presented above can be used in low-cost home systems to simultaneously monitor for leakages from refrigerators, dishwashers, clothes washers, sinks, etc., thereby containing a leakage monitoring network.

Water Vessels: Clearly, this system can monitor for leakages within any type of water vessel; from a fleet of rowboats to cruise ships and ocean liners—all at a low cost, compactness and high level of reliability.

Motor Vehicle Parking Spot Monitors: By using a collection tray below a parked motor vehicle, a low cost leak detector can monitor for water, oil and/or gasoline leaks in parking spaces and/or garages.

Rain Monitor: In some applications (gardens, etc.) it may be desirable to monitor for rain.

Liquid tanks and pipelines: It can also be used, with a Wi-Fi linkage, instead of Bluetooth, to monitor for leakages along any number of large liquid tanks in open fields and/or along miles of liquid-carrying pipelines.

The advantages of the invention include:

1. A 24-hour discreet incontinence detection system (urinary and/or fecal).

2. A single transistor leakage detector circuit; which offers extremely low-cost, virtually zero current drain in standby, can simultaneously handle multiple inputs, and affords high reliability due to its inherent simplicity.

3. A sensor with no moving parts.

4. An easily cleaned sensor.

5. A sensor which is re-usable innumerable times.

6. Incorporates a LED to indicate when the sensor is wet or sufficiently dry.

7. Can monitor entire post-operation patient rooms in hospitals for both blood leakage and/or incontinence leakage—urinary and fecal.

8. Can be used with Wi-Fi linkages to monitor miles of liquid conveying pipelines.

9. Can be used in homes to monitor leakages from any liquid carrying appliance.

10. Can be used in fields or lots which contain liquid tanks.

11. Can be used in all types of water borne vessels.

12. Can be used in attics and basements.

13. Can be interfaced to computers, for medical research projects.

The designs above show only two sensor input ports RG1 and RG2, but by using hubs (passive parallel N-input-wired port devices which feed into a single output port) may be used, and if used in a tree-network (hubs connected in series), there is no practical limit as to how many sensors can feed into one leakage detector circuit.

The invention claimed is:

1. A 24-hour incontinence detection system, comprising:
a DC powered sensor assembly containing a moisture sensor for measuring a resistance value, being a passive device and disposed in an area where a leak is to occur, a liquid leak detection circuit connected to said moisture sensor and receiving the resistance value sensed by said moisture sensor, and a Bluetooth transmitter connected to said liquid leak detection circuit and transmitting a signal being representative of an output of said liquid leak detection circuit;
said liquid leak detection circuit formed of only one transistor connectable to a DC voltage source and having a base node, an emitter node and a collector node, an input connected to said moisture sensor and having first and second connector points, a first resistor connected between said transistor and said first connector point, a second resistor connected between said transistor and ground, and one Zener diode; and
an alarm coupled to said sensor assembly and receiving the signal via said Bluetooth transmitter, said alarm being activated in dependence on the signal.

2. The 24-hour incontinence detection system according to claim 1, wherein said moisture sensor has two metal plates with a gap disposed between said two metal plates, said gap and any liquid disposed in said gap defining the resistance value.

3. The 24-hour incontinence detection system according to claim 2, wherein said moisture sensor has two conductor cables connected to said liquid leak detection circuit and over said two conductor cables said liquid leak detection circuit receives the resistance value.

4. The 24-hour incontinence detection system according to claim 1, further comprising a Bluetooth receiver connected to said alarm and receiving the signal from said Bluetooth transmitter.

5. The 24-hour incontinence detection system according to claim 1, wherein said sensor assembly has a circular shaped, non-conductive substrate being less than 1 inch in diameter and supporting all components of said sensor assembly.

6. The 24-hour incontinence detection system according to claim 5, wherein said circular shaped, non-conductive substrate has a back side opposite a component side, said back side having hook-and-loop material for assisting in attaching said sensor assembly to an undergarment.

7. The 24-hour incontinence detection system according to claim 1, wherein said alarm is selected from the group consisting of a cell phone, a smartphone, a vibrator and a sound box.

8. The 24-hour incontinence detection system according to claim 1, wherein said moisture sensor is one of two moisture sensors connected to said liquid leak detector circuit.

9. The 24-hour liquid leak detection system according to claim 1, wherein said moisture sensor is a passive conductivity wetness sensor functioning as a variable resistor in said liquid leak detection circuit, said variable resistor having two metal plates with a gap disposed between said two metal plates, said gap and any liquid disposed in said gap defining the resistance value.

10. A 24-hour incontinence detection system for detecting an urine leak, comprising:
a DC powered sensor assembly containing a wetness-dependent sensor, said DC powered sensor assembly to be placed where a urine leak is to occur and outputting a variable resistance, said wetness-dependent sensor having an input;
a single transistor detector circuit receiving the variable resistance, said single transistor detector circuit outputting a signal being a 0 VDC signal when said input of said wetness-dependent sensor is dry and the signal rising sharply to a high DC voltage level, being higher than the 0 VDC signal, when said input of said wetness-dependent sensor reaches a pre-set threshold value;
a Bluetooth transmitter having an input receiving the signal from said single transistor detector circuit, said Bluetooth transmitter providing no radio-frequency (RF) output when said input of said Bluetooth transmitter is at 0 VDC, and producing an RF signal when said input of said Bluetooth transmitter is at the high DC voltage level;
an alarm; and
a Bluetooth receiver for sensing the RF signal, said Bluetooth receiver having an output connected to said alarm and activating said alarm upon sensing the RF signal, indicating that the urine leak has been detected.

* * * * *